US009371759B2

(12) United States Patent
Giechaskiel et al.

(10) Patent No.: US 9,371,759 B2
(45) Date of Patent: Jun. 21, 2016

(54) METHOD AND DEVICE FOR DETERMINING THE CONCENTRATION OF AEROSOLS IN HOT GASES, PARTICULARLY IN EXHAUST GASES OF INTERNAL COMBUSTION ENGINES

(75) Inventors: Barouch Giechaskiel, Ranco (IT); Alexander Bergmann, Graz (AT)

(73) Assignee: AVL List GmbH, Graz (AT)

(*) Notice: Subject to any disclaimer, the term of this patent is extended or adjusted under 35 U.S.C. 154(b) by 133 days.

(21) Appl. No.: 14/344,173

(22) PCT Filed: Sep. 11, 2012

(86) PCT No.: PCT/EP2012/067723
§ 371 (c)(1),
(2), (4) Date: Oct. 31, 2014

(87) PCT Pub. No.: WO2013/037765
PCT Pub. Date: Mar. 21, 2013

(65) Prior Publication Data
US 2015/0075135 A1  Mar. 19, 2015

(30) Foreign Application Priority Data
Sep. 12, 2011 (AT) ................ A 1300/2011

(51) Int. Cl.
*F01N 3/00* (2006.01)
*F01N 3/20* (2006.01)
(Continued)

(52) U.S. Cl.
CPC ............ *F01N 3/2006* (2013.01); *F01N 3/021* (2013.01); *F01N 3/0205* (2013.01); *F01N 11/00* (2013.01);
(Continued)

(58) Field of Classification Search
USPC .......... 60/274, 287, 288, 292, 295, 297, 300, 60/311
See application file for complete search history.

(56) References Cited

U.S. PATENT DOCUMENTS

| 4,257,258 A | 3/1981 | Bovenlander |
| 4,449,816 A | 5/1984 | Kohsaka et al. |

(Continued)

FOREIGN PATENT DOCUMENTS

| JP | 6289004 | 10/1994 |
| JP | 2010249754 | 11/2010 |

(Continued)

OTHER PUBLICATIONS

English Abstract of JP 2010249754.
(Continued)

*Primary Examiner* — Binh Q Tran
(74) *Attorney, Agent, or Firm* — Dykema Gossett PLLC

(57) ABSTRACT

For a method for determining the concentration of aerosols in hot gases, particularly in exhaust gases of internal combustion engines, the removal of volatile and semi-volatile particles by heating the exhaust gas is provided, as well as the measurement of the concentration of the aerosols, optionally in a partial flow of an optionally diluted exhaust gas flow.

In order to enable precise measurements of the aerosol concentration in the exhaust gas with lower energy consumption, the exhaust gas is divided in a first stage into two partial flows, both of which are heated, with one of the partial flows being filtered at least once, preferably before heating, and the two partial flows are subsequently recombined. In a second stage, the exhaust gas is again divided into two partial flows, with one of the partial flows being heated even further than in the first stage, and with the other partial flow being filtered at least once. The two partial flows are subsequently recombined, and the concentration measurement is performed on the combined total flow.

15 Claims, 1 Drawing Sheet

(51) Int. Cl.
*F01N 3/02* (2006.01)
*G01N 1/22* (2006.01)
*G01N 15/02* (2006.01)
*F01N 3/021* (2006.01)
*F01N 11/00* (2006.01)

(52) U.S. Cl.
CPC .......... *G01N 1/2252* (2013.01); *G01N 15/0272* (2013.01); *F01N 2560/05* (2013.01); *Y02T 10/20* (2013.01)

(56) References Cited

U.S. PATENT DOCUMENTS

| | | | |
|---|---|---|---|
| 5,279,146 A | | 1/1994 | Asano et al. |
| 5,903,338 A | | 5/1999 | Mavliev et al. |
| 6,796,165 B2 | * | 9/2004 | Abdul-Khalek .... F02D 41/1467 73/114.69 |
| 6,833,028 B1 | | 12/2004 | Scheer et al. |
| 6,962,090 B2 | | 11/2005 | McDonald et al. |
| 7,334,401 B2 | | 2/2008 | Cheng |
| 7,427,311 B2 | | 9/2008 | Burtscher et al. |
| 7,647,810 B2 | | 1/2010 | Wei et al. |
| 7,682,426 B2 | | 3/2010 | Burtscher et al. |
| 8,234,858 B2 | * | 8/2012 | Konstandopoulos F01N 13/0093 60/311 |
| 8,261,540 B2 | | 9/2012 | Konstandopoulos et al. |
| 8,505,276 B2 | * | 8/2013 | Nakamura .............. F01N 11/00 60/276 |
| 8,667,784 B2 | * | 3/2014 | Suzuki .................... F01N 3/023 60/295 |
| 8,820,138 B2 | * | 9/2014 | Dickow ................ G01M 15/02 73/23.31 |
| 2007/0131038 A1 | | 6/2007 | Wei et al. |

FOREIGN PATENT DOCUMENTS

| | | |
|---|---|---|
| JP | 2010261938 | 11/2010 |
| WO | 2007067822 | 6/2007 |

OTHER PUBLICATIONS

English Abstract of JP 2010261938.
English Abstract of JP 6289004.

* cited by examiner

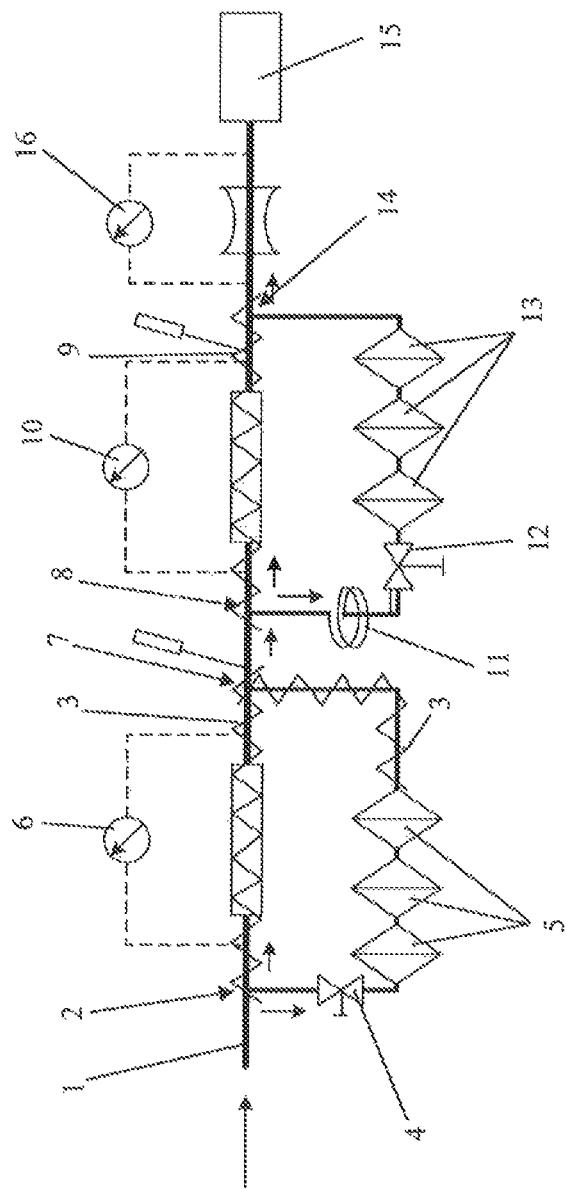

METHOD AND DEVICE FOR DETERMINING THE CONCENTRATION OF AEROSOLS IN HOT GASES, PARTICULARLY IN EXHAUST GASES OF INTERNAL COMBUSTION ENGINES

BACKGROUND AND SUMMARY OF THE INVENTION

The invention relates to a method for determining the concentration of aerosols in hot gases, particularly in exhaust gases of internal combustion engines, the removal of volatile and semi-volatile particles by heating the exhaust gas, as well as measuring of the concentration of the aerosols, optionally in a partial flow of an optionally diluted exhaust gas flow, as well as a device for executing the method, comprising a subsystem for removing volatile and semi-volatile particles by heating the exhaust gas, as well as a measurement system for measuring the concentration of the aerosols, optionally with a device for dividing a partial flow of the exhaust gas flow into the measurement system, as well as, optionally, a system for diluting the exhaust gas flow.

In order to determine the aerosol concentration in the exhaust gas of internal combustion engines, as well as for testing and research purposes and for checking for legal specifications, certain process sequences are necessary in order to provide accurate information. Basic process sequences have even found their way into legislation.

Typically, a hot dilution is performed in which volatile and semi-volatile particles are removed in a heated pipe with wall temperatures between 300 and 400° C. This system is referred to as a "Volatile Particle Remover (VPR)." The concentration of the aerosols is then determined using a particle counter whose inlet temperature should be no greater than 35° C.

Depending on the displacement and/or output of the internal combustion engine, the "volatile particle remover" draws its samples from a full or partial flow dilution system. For research purposes, a sample is often also drawn directly from the exhaust system.

The drawback of all of these systems is their high energy consumption, for which reason they are not well suited to on-board measurement systems. What is more, such systems require an external pressurized air supply; they work with high sample flow rates, which is problematic especially for partial flow dilution systems, and the flow rates in the system overall are very high, which further contributes to the high energy consumption.

It was therefore the object of the present invention to provide an improved method and a device suited to same which avoids the abovementioned drawbacks and enables precise measurements of the aerosol concentration in the exhaust gas of internal combustion engines with low energy consumption.

To achieve this object, the method described at the outset is characterized in that, in a first stage, the exhaust gas is divided into two partial flows, both of which are heated, with one of the partial flows being filtered at least once, preferably before heating; that the two partial flows are subsequently recombined; that, in a second stage, the exhaust gas is again divided into two partial flows, with one of the partial flows being heated even further than in the first stage, and with the other partial flow being filtered at least once; and that the two partial flows are subsequently recombined, and the concentration measurement is performed on the total flow.

According to a first advantageous embodiment, a provision is made that both partial flows are heated to at least 150° C. in the first stage.

Advantageously, the unfiltered partial flow is heated to at least 300° C. in the second stage.

Another, optional feature of the invention is that the unheated partial flow is cooled before the first filtering in the second stage.

According to another embodiment of the invention, a provision is made that the unheated partial flow is cooled to a temperature that does not exceed a temperature of 35° C. after recombination of the partial flows.

Preferably, a provision can also be made that throughput measurements are performed in the unfiltered partial flow, and preferably in the combined total flow as well.

To achieve the abovementioned object, the device described at the outset is characterized by a first branching piece for dividing the exhaust gas into two partial flows, heating devices for both partial flows, and at least one filter device in one of the partial flows, preferably before the heating device; furthermore by a combining piece in which the two partial flows are brought together; furthermore by a second branching piece arranged downstream from the combining piece for dividing again into two partial flows, with another heating device being provided for one of the partial flows and at least one additional filter device being provided in the unheated partial flow; and furthermore by a second combining piece before the measurement system, in which combining piece the two partial flows are subsequently recombined.

According to an advantageous embodiment of this device, a cooling device is arranged after the first combining piece and before the or before each filter device.

Another advantageous embodiment of the device is characterized by throughput measurement devices between at least one branching piece and the following combining piece, each in the unfiltered partial flow.

In such a device, an additional throughput measurement device can also advantageously be present between the last combining piece and the measurement system.

BRIEF DESCRIPTION OF THE FIGURE

In the following description, the invention will be explained in further detail with reference to a schematic exemplary embodiment, in the attached FIGURE.

DETAILED DESCRIPTION OF THE EMBODIMENTS

The exhaust gas of an internal combustion engine is fed to the system according to the invention via a line 1 and then arrives at a first branching piece 2, where the exhaust gas is divided into two (first and second) partial flows. Both partial flows are heated by means of heating devices 3, for example pipes with heated walls, typically to a temperature of at least 150° C. In one of the pipes, a valve 4 for adjusting the dilution ratio is preferably provided before the heating device 3, as well as three filters 5, for example, which separate off moisture, hydrocarbons and certain particles. However, any filter arrangement could also be used that has only one or two of said filters. A throughput measurement device 6, for example functioning according to the capillary principle, is used in the line of the unfiltered partial flow.

After filtering and throughput measurement, the separate partial flows are recombined by the combining piece 7 in order to be divided again into two (third and fourth) partial flows shortly thereafter by a downstream second branching piece 8. For one of the two partial flows, another heating device 9 is provided again after the branching piece 8 which heats this unfiltered partial flow to at least 300° C. so that all volatile and semi-volatile particles are then removed. Another throughput measurement device 10, for example one that also functions according to the capillary principle, is again used in the line of the unfiltered partial flow.

The unheated partial flow is preferably cooled by a cooling device 11 placed into the pipe for that purpose before it, after passing through a valve 12 in order to enable adjustment of the dilution ratio here as well, passes through at least one filter 13. Preferably, three filters 13 are also provided here, in turn, that separate off moisture, hydrocarbons and certain particles.

In a second combining piece 14, the hot partial flow after the throughput measurement and the unheated, filtered and preferably cooled partial flow are then recombined, and the total flow is fed to the measurement system 15 which, in principle, can function in any manner but preferably has a pump in order to suck the exhaust gas through the system. The cooled partial flow is advantageously brought by the cooling device 11 to a temperature which is such that the combined total flow does not exceed a temperature of 35° C. If necessary, another throughput measurement device 16 can also be provided for the total flow.

The invention claimed is:

1. A method for determining a concentration of aerosols in a hot gas comprising the steps of:
   (a) dividing a flow of hot gas containing aerosols into first and second partial gas streams,
   (b) heating each of the first and second partial gas streams,
   (c) filtering the second partial gas stream,
   (d) recombining the first and second partial gas streams,
   (e) dividing the recombined first and second partial gas streams from step (d) into third and fourth partial gas streams,
   (f) heating the third partial gas stream to a temperature higher than either of the first and second partial gas streams are heated in step (b),
   (g) filtering the fourth partial gas stream,
   (h) recombining the third and fourth partial gas streams to provide a recombined total gas stream, and
   (i) measuring a concentration of aerosols in the recombined total gas stream of step (h).

2. The method according to claim 1, wherein the hot gas containing aerosols comprises an exhaust stream from an internal combustion engine.

3. The method according to claim 1, wherein step (c) occurs before heating of the second partial gas stream in step (b).

4. The method according to claim 1, wherein in step (b) each of said first and second partial gas streams are heated to at least 150° C.

5. The method according to claim 1, wherein in step (f) the third partial gas stream is heated to at least 300° C.

6. The method according to claim 1, including between steps (f) and (g) a step of cooling the fourth partial gas stream.

7. The method according to claim 6, wherein the fourth partial gas stream is cooled before being filtered.

8. The method according to claim 6, wherein the fourth partial gas stream is cooled to a temperature such that the recombined total gas stream has a temperature which does not exceed 35° C.

9. The method according to claim 1, including a step of measuring a throughput of said first partial gas stream.

10. The method according to claim 1, including a step of measuring a throughput of said third partial gas stream.

11. An apparatus for determining concentration of aerosols in a hot gas comprising:
    an aerosol measurement system, and
    a subsystem for delivering a flow of hot gas containing aerosols to said aerosol measurement system and for removing volatile and semi-volatile particle from the flow of hot gas, said subsystem comprising:
      a line for delivering a stream of hot gas containing aerosols to a first branching element for dividing said stream into first and second partial gas streams, first and second heating devices for heating said respective first and second partial gas streams, a filter device in the second partial gas stream, a first combining element for recombining the first and second partial gas streams, a second branching element downstream of the first combining element for dividing said recombined first and second partial gas streams into third and fourth partial gas streams, a third heating device for heating the third partial gas stream, an additional filter device in the fourth partial gas stream, and a second recombining element for recombining the third and fourth partial gas streams into a recombined total gas stream for delivery to the aerosol measurement system.

12. The apparatus according to claim 11, including a cooling device for cooling the fourth partial gas stream upstream of the additional filter device.

13. The apparatus according to claim 11, including a first throughput measuring device for measuring flow rate of said first partial gas stream.

14. The apparatus according to claim 11, including a second throughput measuring device for measuring flow rate of said third partial gas stream.

15. The apparatus according to claim 14, including a third throughput measuring device for measuring flow rate of said recombined total gas stream.

* * * * *